United States Patent [19]

Klevan

[11] Patent Number: 5,302,510
[45] Date of Patent: Apr. 12, 1994

[54] DNA SIZING CONTROL STANDARDS FOR ELECTROPHORETIC ANALYSES

[75] Inventor: Leonard Klevan, Gaithersburg, Md.

[73] Assignee: Life Technologies, Inc., Gaithersburg, Md.

[21] Appl. No.: 918,765

[22] Filed: Jul. 27, 1992

[51] Int. Cl.$^5$ ............................................. C12Q 1/68
[52] U.S. Cl. .................................... 435/6; 435/967;
  436/8; 536/23.1; 935/78
[58] Field of Search ................ 536/27; 435/5, 6, 967;
  436/8; 935/78

[56] References Cited

U.S. PATENT DOCUMENTS

| | | | |
|---|---|---|---|
| 4,771,384 | 9/1988 | Daniels et al. | 364/413.01 |
| 5,030,566 | 7/1991 | Son et al. | 435/91 |

FOREIGN PATENT DOCUMENTS

| | | |
|---|---|---|
| 0466404 | 1/1992 | European Pat. Off. |
| 63-113359 | 5/1988 | Japan |

OTHER PUBLICATIONS

Carman et al., Detection of Enzymatically Amplified Human Immunodeficiency Virus DNA by Oligonucleotide Solution Hybridization and by Incorporation of Radio- . . . , *J. Clin. Microbiol.* 27:2570–2573 (1989).

Gralla, J. D., Rapid "footprinting" on supercoiled DNA, *Proc. Natl. Acad. Sci. USA* 82:3078–3081 (1985).

Molecular and Cell Biology 1990 Price List, p. 23, Pharmacia Inc.

Product insert for DNA Analysis Marker System, marketed by GIBCO BRL, available in 1990.

Bernards et al., Pulsed field gradient electrophoresis of DNA digested in agarose allows the sizing of the large duplication unit of a surface . . . , *Chem. Abstr.* 105:187 Abstract No. 92470r (1986).

Budowle et al., Modifications to improve the effectiveness of restriction fragment length polymorphism typing, *Applied and Theoretical Electrophoresis* 1:181–187 (1990).

Huang et al., Restriction endonuclease analysis of granulosis virus DNA of Agrotis exclamationis Linnaeus, *Chem. Abstr.* 107:175 Abstr. No. 34093a (1987).

Jones et al., Separation of yeast chromosomes in the megabase range suitable as size markers for pulsed-field gel electrophoresis, *Chem. Abstr.* 112:172 Abtr. No. 230760h (1990).

Mathew et al., High-Resolution Separation and Accurate Size Determination in Pulsed-Field Gel Electrophoresis of DNA. 1. DNA Size Standards and the Effect . . . , *Biochemistry* 27:9204–9210 (1988).

Promega 1990–1991 Catalog, Chromosomal DNA Analysis 278–279.

Rickwood et al., "Practical Approaches in Biochemistry Series" IRL Press Oxford, pp. 227–232 (1990).

Waterbury et al., Generation of lambda phage concatemers for use as pulsed field electrophoresis size markers, *Nucleic Acids Research* 15(9):3930 (1987).

English Abstract of European Patent Publication 0 357 028 published Mar. 7, 1990.

1991 Life Technologies Inc. Catalog, p. 325.

*Primary Examiner*—Amelia Burgess Yarbrough
*Assistant Examiner*—Kenneth Horlick
*Attorney, Agent, or Firm*—Sterne, Kessler, Goldstein & Fox

[57] ABSTRACT

The present invention is directed to a method for assessing the reliability of DNA sizing measurements performed on DNA samples. DNA sizing control standards are disclosed wherein each standard contains a unique set of DNA restriction fragments composed of coding fragments and measuring fragments of known sizes. Methods for constructing the fragments which can be used in making the DNA sizing control standards are disclosed. Kits comprising the DNA sizing control standards of the present invention are also disclosed.

10 Claims, No Drawings

DNA SIZING CONTROL STANDARDS FOR ELECTROPHORETIC ANALYSES

FIELD OF THE INVENTION

The present invention is in the field of molecular biology and DNA based identification of individuals and relates to the technique of gel electrophoresis of nucleic acid fragments. More specifically, the invention relates to the use of DNA fragments of known molecular weight to assess the reliability of DNA sizing measurements on DNA samples.

BACKGROUND OF THE INVENTION

Gel electrophoresis is a technique that is commonly employed in molecular biology for determining the size distribution of restriction enzyme digests of DNA. This technique has found widespread use in research, as well as in practical applications. It has been found that certain DNA banding patterns detectable by electrophoresis are often associated with specific disease states. Thus, the electrophoretic analysis of samples obtained from a patient may allow physicians to make or confirm a particular diagnosis.

Other applications have resulted from the fact that DNA samples obtained from a particular individual can be digested with restriction enzymes, the fragments separated by electrophoresis and the resulting pattern of bands used to unambiguously identify that particular individual (except in the case of identical twins). Consequently, the electrophoretic analysis of DNA is finding application in the area of law enforcement. A person convicted of a crime may have a sample taken for DNA analysis. The results of this "DNA fingerprint" are compared to evidentiary material found at the scene of a crime or are kept on record and used for future comparison in much the same way as conventional fingerprints.

However, because the resulting data will be used in courts of law, the identification of individuals by DNA fingerprinting is technically demanding and must be done by laboratories with specialized equipment and personnel. This creates a problem of quality control. Specifically, when the electrophoretic positions of DNA bands is critical data and samples are being analyzed on an industrial scale (tens of thousands of samples per year) by independent testing laboratories, it is important to know whether the data reported can be relied upon, i.e., do the results reported accurately represent the banding pattern as it should appear if all of the steps in the analysis had been correctly performed. The present invention is specifically aimed at addressing this problem.

SUMMARY OF THE INVENTION

The present invention is directed to solving the problem of determining the reliability of electrophoretic analysis data performed on DNA restriction enzyme digests. The invention consists of DNA sizing control standards and a method for use thereof which can be used to assess the reliability of data obtained from enzyme restriction digests of DNA samples.

The DNA sizing control standards of the present invention contain various combinations of DNA fragments of defined size. They are made by digesting DNA with one or more restriction endonucleases in such a way that each fragment contains a common sequence element capable of hybridizing to an oligonucleotide probe. Each standard comprises a unique set of these fragments. Fragments may be either measuring fragments, coding fragments, or both. Coding fragments are used to unambiguously identify the sizing control standard, while measuring fragments are used to evaluate the accuracy of the sizing measurement.

The present invention, as exemplified herein, employs specific restriction endonucleases that can be used for generating fragments of appropriate size from the DNA of bacteriophage λ (lambda). DNA fragments are typically generated in such a way that the range of sizes cover the expected range of the sample data.

DNA sizing control standards may be supplied as part of a kit in which standards take the form of premixed combinations of measuring fragments and coding fragments that are supplied together with an oligonucleotide probe complementary to one or both of the measuring and coding fragments. The kit may also include an enzyme capable of labeling the probe either radioactively or in some other way which will allow visualization of electrophoretic bands. Examples of enzymes that could be used for labeling include DNA polymerases (for example $E.$ $coli$ DNA polymerase I) or polynucleotide kinase. Alternatively, kits may include DNA sizing standards along with some means for making a probe. For example, RNA probes could be made by supplying a DNA strand containing a sequence element corresponding to the probe sequence which is under the control of a promoter recognized by RNA polymerase. The RNA polymerase itself may or may not be included with the promoter/probe constructs.

The present invention is also directed to a method for determining the reliability of DNA electrophoretic results. This method is referred to as a "DNA sizing control system" and comprises preparing DNA sizing control standards as described herein and using these in conjunction with the DNA samples to be tested. DNA samples are electrophoresed on the same gels as the DNA sizing control standards. A comparison is then made between the results empirically obtained for the standards and the expected results. If the observed and expected band positions of the DNA sizing control standards agree with one another, the data derived from that analysis may be considered as reliable.

The fragments used in the DNA sizing control system are designated as either "coding fragments" or "measuring fragments". Each individual standard contains a specific set of coding fragments which serves to identify that standard. Each set of coding fragments has associated with it a different combination of measuring fragments. It is expected that such standards will be especially useful to users who perform a very large number of electrophoretic analyses and who must therefore have available, and be able to keep track of, a correspondingly large number of unique standards. In order to obtain the most reliable results, it is preferred that the individual actually performing the electrophoresis not be aware of the results that are expected for the standards. Such an individual may either be supplied with separate standards and samples or the DNA standards may be incorporated into the samples themselves. In the latter case, it is preferred that the measuring fragments within the DNA sizing control standards be distinguishable from sample DNA fragments based upon the ability of the measuring fragments to hybridize to a specific oligonucleotide probe.

It is expected that the DNA sizing control standards and the DNA sizing system described herein will be useful to research laboratories, law enforcement agencies, and anyone else engaged in analyzing DNA samples on a large scale and needing to check on the accuracy of electrophoretic results.

DETAILED DESCRIPTION OF THE INVENTION

A. Definitions

As used herein and unless otherwise indicated, the term "DNA fingerprinting" refers to the procedure whereby DNA samples are taken from a group of individuals, e.g., those convicted of a felony; the DNA is digested with a restriction enzyme; the size distribution of the resulting fragments is determined by gel electrophoresis. The data for each individual may be kept on file and compared with data obtained from future samples for the purpose of identification.

The term "DNA sizing control standards" refers to a set of DNA fragments of known molecular weight, each combination of fragments constituting a unique standard. Standards are comprised of coding DNA fragments and measuring DNA fragments and are analyzed by electrophoresis at the same time as are samples containing DNA fragments of unknown size. If the electrophoretic positions obtained for the fragments in the standard correspond to the expected positions, this is taken as an indication that the sizing of the data concurrently obtained is reliable.

The term "measuring fragments" refers to the DNA fragments which are combined to form sizing control standards. Measuring fragments are prepared so that their molecular weights are known and can be used to test the accuracy of sizing data. Measuring fragments hybridize to a specific oligonucleotide probe. In order to be clearly resolved by electrophoresis, measuring fragments should differ by a measure of at least 5%.

"Coding fragments" are defined as DNA fragments arbitrarily chosen to be used for identifying the particular standard. Such fragments should differ in size by a measure of at least 5%. These fragments may be obtained from the same set of fragments as the measuring fragments (defined above) or they may be selected from a distinct set of fragments. In general, coding fragments may have an arbitrary, irregular spacing when separated by electrophoresis. In a most preferred embodiment, coding fragments are a fraction of a number of regularly spaced fragments, e.g., one to four fragments out of a set of five regularly spaced fragments.

The term "probe" refers to a nucleic acid molecule, e.g., an oligonucleotide, with a sequence complementary to a sequence element found within DNA sizing fragments. Preferably the probe DNA is labeled or otherwise detectable and used to visualize DNA bands after electrophoresis.

B. Sizing Control Standards

The present invention is directed to the use of DNA sizing control standards used for electrophoresis. Each standard contains a unique set of pooled DNA restriction fragments of various sizes and each of these fragments contains at least one "S" sequence complementary to an oligonucleotide probe. The fragments may be identified after electrophoresis by Southern blotting and hybridization.

A number of mixtures of nucleic acid fragments are commercially available that can be used as size markers. The technology described in European Patent Application No. 466,404 (priority based on U.S. patent application Ser. No. 07/552,406, filed Jul. 13, 1990, by Carlson, Watkins and Klevan, for "Size Markers For Electrophoretic Analysis of DNA", the contents of which is fully incorporated by reference herein), allows the construction of DNA marker ladders in which each band of the ladder is of known molecular weight and all "target" bands are visualized by hybridization to a specific, labeled oligonucleotide probe. An example of the application of this technology may be found in the "DNA Analysis Marker System" sold by Life Technology, Inc., Gaithersburg, Md. In this system, thirty restriction enzyme digests of lambda DNA are produced with different enzymes or combinations of enzymes. The DNA fragments produced by the restriction digests are pooled, separated by electrophoresis and individual bands are visualized with an appropriately labeled oligonucleotide probe of known sequence. This probe will identify thirty bands within the pooled digests, and these bands exhibit a near logarithmic distribution on gels. This technology allows one to construct combinations of marker bands within gels which are highly reproducible and specific, yet which offer great combinatorial flexibility in choice of banding patterns.

The preferred embodiments of the present invention rely upon the flexibility in application Ser. No. 07/552,406 and represent a new application thereof. Specifically, one may use the same probe to detect both size markers and sizing control fragments. Furthermore, one may use the same technology to make sizing control fragments and marker fragments. By combining the DNA fragments in unique combinations, standards have been developed which can be used to check on the quality of electrophoretic sizing data. For example, a purchaser of the standards may receive vials, each vial containing a set of DNA fragments and information on the electrophoretic pattern that should be exhibited by the standard. The purchaser could then use the standards directly or, more typically, supply the standard to an end-user who is electrophoretically analyzing samples supplied by the purchaser and who would not be informed of the pattern that should be exhibited by the standard. The purchaser could then determine the reliability of the results reported by the end-user by seeing if the data reported for the standard is accurate to within a certain tolerance. Thus, if all standard bands were reported to have sizes which were within a given percentage, e.g., 2.5%, of what was expected, the data for both the standard as well as the samples might be deemed as reliable.

There are certain variations on the way in which sizing control standards are used which are clearly encompassed by the present invention. For example, DNA samples and standards may be analyzed in separate lanes of a gel, or standards and samples may be combined and analyzed together. If samples and standards are combined, then it is preferred that the "S" sequence recognized by the probe be unique to the marker bands. As a result, only marker bands would be visualized after hybridization with the appropriate probe even though sample DNA fragments are present in the same gel lane. A purchaser may or may not supply an end-user with the probe necessary for visualizing the marker fragments. Hybridization of the gel run by the end-user could then be performed either by the purchaser or by a separate laboratory.

Purchasers of DNA sizing controls may perform their own electrophoretic analyses and may set their own criteria of acceptability in terms of how closely expected and reported results must agree. DNA marker fragments could potentially be supplied in an uncombined form so that these purchasers can make up their own standards. This might be important for purchasers interested in maintaining an especially high level of confidentiality concerning the outcome of results.

The invention may take the form of a kit comprising a carrier means being compartmentalized to receive in close confinement therewith one or more container means such as vials, tubes and the like. One or more of said containers may contain the marker DNA fragments preferably, but not necessarily, already admixed into standards. One or more separate containers may contain oligonucleotide probes capable of annealing to said DNA fragments. Such a kit may also include one or more separate containers with proteins capable of enzymatically labeling probe DNA, for example, polynucleotide kinase or the Klenow fragment of E. coli DNA polymerase I. Preferably, the probe DNA is supplied as a pair of synthetic oligonucleotides. Each of the probe oligonucleotides are preferably at least 20 nucleotides in length and complementary to one another for 15 to 30 base pairs at their 3' end. Such oligonucleotides can be labeled by incorporation of labeled nucleotides in a chain extension reaction with each oligonucleotide serving as a primer and using the other as a template.

The probe may be labeled with a radioactive isotope (e.g., $^3H$, $^{32}P$, $^{35}S$, or $^{125}I$), a ligand (e.g., biotin), a hapten (e.g., dinitrophenol or fluorescein), or an enzyme (e.g., alkaline phosphatase, $\beta$-galactosidase, horseradish peroxidase, or microperoxidase), or any other suitable labeling material known or discovered in the art.

Containers of a kit of the present invention may alternatively contain a means for making the probe, as opposed to of just a means of labeling probes. RNA probes may be used as well as DNA probes. The means for making the probe may include transcribing probe sequences which are under the control of a promoter. For example, DNA sequences downstream from SP6 promoters may be transcribed in vitro by SP6 RNA polymerase and sequences downstream from T7 promoters may be transcribed in vitro by the T7 RNA polymerase. The polymerases carrying out such transcription may also be included in containers comprising part of the kit.

C. Sizing Control Compositions, Kits and Methods

The invention is directed to a unique method, hereinafter a "sizing control system", which can be used by those needing to determine the reliability of DNA electrophoretic analyses. This system is specifically aimed at addressing problems in the sizing control of DNA fingerprints, where the accuracy of a very large number of results must be assessed. The solution involves supplying internal standards along with the unknown samples. The system of combining coding fragments with measuring fragments described below and in Example 2 allows for the development of a very large number of different standards. This insures that testing laboratories will be unaware of the banding patterns expected from the supplied standards. Thus, the integrity of results is further insured.

The system disclosed in the present invention is highly flexible. In a preferred embodiment, each DNA sizing control standard contains a unique set of coding DNA fragments. Coding fragments are selected from a group of markers made as described in Example 1. The presence or absence of a coding band is represented by a binary code (e.g., "1" if the band is present and "0" if the band is absent).

Coding fragments may represent all of the bands in a particular region of the gel or in multiple regions. Since the coding fragment region will lack one or more bands, those bands designated as coding fragments are not present in regions where sample fragments are concentrated so as to maximize the accuracy of the sample measurement. Each set of coding fragments has associated with it one or more measuring fragments. Measuring fragments may be selected from a group of markers distinct from the markers from which coding fragments are selected. In this case, coding bands and measuring bands may hybridize to different probes. Alternatively, one group of markers may be used, with certain markers designated as coding fragments and others as measuring fragments.

In another embodiment, the measuring bands themselves serve as coding fragments. All bands are measured. The size of each band is then compared with the known sizes of bands that have been placed together in sets. If any band size does not correspond, within tolerances, to bands that have been put in the set, the data may be rejected. If all the band sizes correspond to those placed in sets, but the combination of bands is not one that has been assembled, the data may similarly be rejected.

For example, suppose a group of fragments is generated according to the methods of Example 1 in which there are 10 bands from 1 to 10 kbp in length and where each fragment is 1 kbp larger than its predecessor. Bands electrophoresing at positions characteristic of DNA fragments with molecular weights of 1, 2, 3, 4 and 5 kbp are designated as coding bands and are used in combination with measuring bands with electrophoretic positions of 6 through 10 kbp. Any combination of coding bands and measuring bands could be used to construct a standard with a unique recognition pattern. Thus, one standard could be obtained by combining coding fragments of 2 and 5 kbp in length with measuring fragments 6 and 8 kbp in length. Using a binary system, the coding number of the standard would be 01001 (since the 1, 3 and 4 kbp coding bands are missing).

Once a group of standards has been made, a party practicing the sizing control system of the present invention would typically supply an end-user, e.g., a testing laboratory, with the DNA samples to be tested along with one or more sizing control standards. The DNA samples may be subjected to one or more restriction digests by the end-user, or the DNA may be digested before it is given to the end-user. Alternatively, the polymerase chain reaction ("PCR") may be used to generate DNA strands from samples. PCR generated strands may be electrophoresed directly or digested with one or more restriction enzymes prior to electrophoresis. Although the expected electrophoretic results for the sizing control standard would be known by the party practicing the sizing control system, such information should not be supplied to the end-user. In the example given above, standard 01001 would be given to independent testing laboratories along with samples to be analyzed.

In the next step of the present invention, the end-user would analyze the DNA samples and standards electrophoretically and report the results to the party practicing the sizing control system. In order for reported results to be considered as reliable, the testing laboratory would have to report correct electrophoretic positions for the coding bands as well as correct positions for the measuring bands. How closely reported and expected results must be in order for the data to be acceptable would be a matter of choice for the user of the sizing control system.

In understanding the present invention, it may be helpful to consider the following general example of how it might be used. The example relates to establishing a data bank containing the restriction patterns, i.e., the DNA fingerprints, of all convicted felons. A large number of DNA samples, at least one sample for each felon, could be sent to testing laboratories. The laboratories then perform appropriate restriction digests and report back to the agency the electrophoretic size distribution of the resulting fragments. In order to determine if the results being reported are reliable, the Sizing Control System disclosed herein is employed. Sizing control standards are supplied along with the samples, each standard containing the coding and measuring bands described above. The testing laboratory may also be supplied with the oligonucleotide probe needed to visualize the measuring bands and coding bands. Each time that the testing laboratory analyzed a sample, it would also analyze the measuring bands and coding bands of one or more standards. Since the sizes of the standard marker bands are known, it can be determined if the results reported for those standards are accurate and, by extension, whether the sizing results reported for other samples are also accurate.

A second way of practicing the present invention's sizing control system is illustrated in Example 3. Instead of separately designating marker bands as either coding bands or measuring bands, a party applying the sizing control system may simply keep a record of expected results for different standards and determine whether the electrophoretic band positions reported by an end-user fall within acceptable tolerances.

Modifications of the above described modes for carrying out the invention that are obvious to persons of skill in molecular biology or related fields are intended to be within the scope of the claimed invention. Although the foregoing invention has been described in detail by way of illustration and example for the purposes of clarity and understanding, it will be obvious that certain changes and modifications may be practiced within the scope of the appended claims.

EXAMPLES

EXAMPLE 1

Construction of Target Fragments to be Used in Sizing Control Standards

A: Common Materials and Methods

*E. coli* bacteriophage λ (lambda) DNA (cIind 1, ts857, Sam 7) which is well-known in the art, having been sequenced and which is commercially available from a number of sources, was the source of all target DNAs. The probe DNA for either of the marker ladders exemplified herein may consist of any DNA from between nucleotides 33,783 and 34,212 of that λ DNA. Oligonucleotides were synthesized using standard phosphoramidite chemistry well-known in the art.

For each digest, λ DNA was cleaved with one or two restriction endonucleases. The enzymes used for individual digests are indicated in Table 1. Digestions were performed under standard conditions, generally according to the instructions of the enzyme's manufacturer. Restriction digests were pooled after digestion.

B: First Method of Constructing a Probe

In the first procedure, the target DNA consisted of pooled equal amounts of 30 different restriction digests of phage λ DNA. The probe DNA was a 26-base oligonucleotide having a sequence of

5'GCGACATTGCTCCGTGTATTCACTCG3' which is complementary to nucleotides 34,000 to 34,025 of the standard λ DNA map. This oligonucleotide was labeled at its 5'-end by T4 polynucleotide kinase and [γ-$^{32}$P]-ATP (BRL cat. no. 8060SA, Life Technologies, Inc., Gaithersburg, Md.). Hybridization of $^{32}$P-labeled probe DNA to a Southern blot of the target DNA revealed bands of the expected pattern.

C: Second Method of Constructing a Probe

The method described in Part B above was improved by changing the probe DNA such that (a) it could easily be labeled with DNA polymerase as well as polynucleotide kinase, and (b) it would remain hybridized to the Southern blot even when washed at high temperature (65° C.) and low salt concentration (0.015M NaCl). This was achieved by utilizing two 70-base, synthetic oligonucleotides that were complementary to opposite strands of λ DNA, and also complementary to one another for 15 bases at their 3'-termini. The two oligonucleotides were as follows:

5'AGGCCACTATCAGGCAGCTTTGTTGTTCTGTTTAC-
CAAGTTCTCTGGCAATCATT<u>GCCGTCGTTCGTATT</u>3'

5'AGCCTGAAGAAATGTTTCCTGTAATGGAAGATGGG-
AAATATGTCGATAAATGGG<u>CAATACGAACGACGGC</u>3'

The underlined segments are complementary to each other. The first oligonucleotide is encoded by sequences from coordinates 34,078 (5'-end) to 34,147 (3'-end) and the second oligonucleotide is encoded by sequences from 34,133 (3'-end) to 34,202 (5'-end) on the standard λ map. These oligonucleotides were mixed with each other, the Klenow fragment of *E. coli* DNA polymerase I, and four deoxynucleotide triphosphates, one of which was α-$^{32}$P-labelled. The polymerase extended each oligonucleotide using the other as a template and produced two α-$^{32}$P-labelled, complementary oligonucleotides. This new probe hybridizes to the same target fragments as the previous probe. A mixture of the new 70-mers was labeled with the large fragment of *E. coli* DNA polymerase I and hybridized to a Southern blot of the target DNA.

In preferred embodiments, one increases the amounts, i.e., relative copy number or the dosage, of the target DNA for the largest and smallest bands. Large DNA fragments blot inefficiently. As is well known in the art, small fragments are poorly retained on membranes during hybridization. Therefore, the signal from large DNA fragments and small DNA fragments tends to be less than the signal from bands in the middle range. Increasing the dose threefold of bands greater than 6000 bp or less than 900 bp has been shown to be advantageous.

TABLE 1

Examples of Possible DNA Target Fragments

| Enzyme(s) | Size | Lambda Coordinates | |
|---|---|---|---|
| | | Left | Right |
| XbaI | 23,994 | 24,508 | 48,502 |
| SstI | 22,621 | 25,881 | 48,502 |
| XhoI | 15,004 | 33,498 | 48,502 |
| NcoI/BglII | 11,919 | 32,329 | 44,248 |
| XbaI/BglII | 11,203 | 24,508 | 35,711 |
| HindIII | 9,416 | 27,479 | 36,895 |
| SmaI | 8,271 | 31,619 | 39,890 |
| EcoRI | 7,421 | 31,747 | 39,168 |
| AvaII | 6,442 | 32,562 | 39,004 |
| HaeII | 5,861 | 28,859 | 34,720 |
| EcoRV/AvaII | 5,415 | 33,589 | 39,004 |
| AvaI | 4,716 | 33,498 | 38,214 |
| AvaII/HindIII | 4,333 | 32,562 | 36,895 |
| BglI/BstEII | 4,045 | 32,329 | 36,374 |
| AvaII/BstEII | 3,812 | 32,562 | 36,374 |
| DraI | 3,599 | 32,705 | 36,304 |
| XhoI/HindIII | 3,397 | 33,498 | 36,895 |
| SmaI/HaeII | 3,101 | 31,619 | 34,720 |
| XhoI/BstEII | 2,876 | 33,498 | 36,374 |
| NciI | 2,650 | 33,158 | 35,808 |
| NdeI | 2,433 | 33,680 | 36,113 |
| MspI | 2,293 | 33,157 | 35,450 |
| XhoI/BglII | 2,213 | 33,498 | 35,711 |
| HincII | 2,015 | 33,246 | 35,261 |
| EcoRV/MspI | 1,861 | 33,589 | 35,450 |
| XhoI/HincII | 1,763 | 33,498 | 35,261 |
| EcoRV/HincII | 1,672 | 33,589 | 35,261 |
| RsaI | 1,568 | 32,868 | 34,436 |
| SspI | 1,431 | 33,572 | 35,003 |
| MspI/BamHI | 1,342 | 33,157 | 34,499 |
| ThaI/RsaI | 1,287 | 33,149 | 34,436 |
| Sau3AI | 1,176 | 33,323 | 34,499 |
| ClaI | 1,112 | 33,585 | 34,697 |
| CfoI | 993 | 33,726 | 34,719 |
| EcoRV/BamHI | 910 | 33,589 | 34,499 |
| HinfI | 844 | 33,783 | 34,627 |
| DdeI | 784 | 33,535 | 34,319 |
| EcoRV/CvnI | 730 | 33,589 | 34,319 |
| HinfI/RsaI | 653 | 33,783 | 34,436 |
| NsiI | 526 | 33,686 | 34,212 |

EXAMPLE 2

Preferred Sizing Control System

The marker fragments generated as described in Example 1 are used to make sizing control standards as follows: For simplicity, there may be 18 marker fragments, each about 1 kbp apart, i.e., there are fragments of about 1 kbp, 2 kbp, 3 kbp, and so on, up to a final fragment of about 18 kbp in length. Bands 1 to 5 are designated as coding fragments, while bands 6 to 18 are measuring fragments. These fragments are combined to form a series of sizing control standards. For example, one standard might have coding bands of 2 and 5 kbp and measuring bands of 8, 9, 13, 16 and 17 kbp. Since only coding bands 2 and 5 are present, this standard would have the coding number of 01001 in a binary system or "9" in a decimal system.

Each time the party practicing the invention supplies a testing laboratory with DNA samples for analysis, it also supplies one or more standards in separate vials. The laboratory analyzes both the standards and the samples and reports back the results. If the size reported for each band in the standard does not fall within a preselected tolerance of what the correct size of that band is known to be, the data would not be relied upon. For example, if the testing laboratory receiving standard 01001 does not report band sizes within a certain tolerance of 8, 9, 13, 16 and 17 kbp (for example, within 2.5% of the known sizes of the fragments), the results reported by that laboratory would not be considered as accurate and would for example, not be entered into a database. Of course, if the sizes of the coding bands were incorrect, the data would also be rejected.

Since five coding fragments would permit only $2^5$ (that is 32) different sizing control test patterns, one could assign test series letters (e.g., "sizing control test standard series A") allowing one to reuse the five coding fragments numerous times.

EXAMPLE 3

Alternative Sizing Control System

An alternative sizing control system would be practiced as in Example 2, but would not use any specific coding bands (e.g., bands 1-5) for identifying standards. Using, as an example, the same patterns as in Example 2 above, the testing laboratory would report the sizes of 7 bands, which the validating authority would compare with a list of fragment sizes known to be present in the various standards. For ease of illustration, assume that the band sizes in kbp are exactly equal to their position number. If the testing laboratory reports that the standard gave bands at 1.97 kbp, 5.04 kbp, 7.9 kbp, 9.05 kbp, 13.1 kbp, 16.3 kbp, and 17.4 kbp, the central authority would compare these results to a sorted list of band size combinations known to be contained in standards:

| <362 | ... |
|---|---|
| #362: | 2, 4, 9, 12, 15, 17, 18 |
| #364: | 2, 5, 7, 12, 13, 17 |
| #365: | 2, 5, 8, 9, 13, 16, 17 |
| #366: | 2, 5, 13, 16, 17, 18 |
| #367: | 2, 6, 7, 10, 17 |
| >367 | ... |

Going down the list, one would see that 1.97 kbp is within 2.5% of the first band and 5.04 kbp is within 2.5% of the second band of patterns 364-366 and that 7.9 kbp, 9.05 kbp, 13.1 kbp, 16.3 kbp, and 17.4 kbp all fall within tolerances of a known sample. Therefore, the unknown data, i.e., the data for the samples being analyzed at the same time as the standards, would be accepted. If the pattern was reported to be 1.97 kbp, 5.04 kbp, 7.9 kbp, 9.05 kbp, 13.1 kbp, 16.5 kbp, and 17.4 kbp, the data would not be accepted, since 16.5 kbp is not within 2.5% of 16 kbp, and there is no pattern in the list that is within tolerances of the reported band sizes. In this case, the rest of the data on the gel would not be accepted.

Another way of analyzing this data would be to convert band patterns to binary numbers. If a target band did not fall within 2.5% of any known target band, the data would be thrown out. Similarly, if the binary number (or its decimal equivalent) did not correspond to a number on the list, the data would be thrown out.

| Bands | | Binary | Decimal |
|---|---|---|---|
| #362: | 2, 4, 9, 12, 15, 17, 18 | 010100001001001011 | 82,507 |
| #364: | 2, 5, 7, 12, 13, 17 | 010010100001100010 | 75,874 |
| #365: | 2, 5, 8, 9, 13, 16, 17 | 010010011000100110 | 75,302 |
| #366: | 2, 5, 13, 16, 17, 18 | 010010000000100111 | 73,767 |
| #367: | 2, 6, 7, 10, 17 | 010001100100000010 | 71,938 |

It should be noted that bands do not necessarily have to be in numerical order, facilitating addition of new bands to the system from time to time. For example:

```
1 2 3 4 5 20 6 7 8 9 10 11 12 19 13 14 15 16 17 18
| | | | |  | | | | | |  |  |  |  |  |  |  |  |  |
```

Bands are preferably spaced at least 2 times the tolerance apart, so that a sizing control number can unambiguously be assigned to a band. Thus, if the tolerance is 2.5%, the bands must be at least 5% different in size. For example, given a tolerance of 2.5% and correct sizes for bands 2 and 3 of 1.00 kbp and 1.04 kbp respectively (4% different), a measurement of 1.02 kbp could not be assigned unambiguously to either band. In contrast, if the correct sizes were 1.00 kbp and 1.06 kbp (6% different), 1.02 kbp would unambiguously be assigned to band 2.

EXAMPLE 4

Preliminary Test of Scheme

Control sets were constructed with three bands each and electrophoresed in the same gel as a marker ladder of "Kit 2" of European Patent Application No. 466,404. The following data were obtained:

| Set | Measured | Actual | Absolute Difference | % Difference |
|-----|----------|--------|---------------------|--------------|
| 1   | 8232     | 8271   | −39                 | −0.47        |
|     | 3397     | 3397   | 0                   | 0            |
|     | 2439     | 2433   | 6                   | −0.25        |
| 2   | 7419     | 7421   | −2                  | −0.03        |
|     | 6469     | 6442   | 27                  | 0.42         |
|     | 2213     | 2213   | 0                   | 0            |
| 3   | 4716     | 4716   | 0                   | 0            |
|     | 2219     | 2213   | 6                   | 0.27         |
|     | 1672     | 1672   | 0                   | 0            |
| 4   | 9490     | 9416   | 74                  | 0.79         |
|     | 3812     | 3812   | 0                   | 0            |
|     | 2015     | 2015   | 0                   | 0            |
| 5   | 4717     | 4716   | 1                   | 0.02         |
|     | 3398     | 3397   | 1                   | 0.03         |
|     | 1573     | 1568   | 5                   | 0.32         |

*% difference = (absolute difference/actual) × 100.
All of the data were within tolerances.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following Claims.

What is claimed is:

1. A method for determining the reliability of electrophoretic DNA sizing measurements comprising:
   a) supplying a sizing standard wherein:
      i) said sizing standard is obtained by pooling more than one measuring DNA fragment and more than one coding DNA fragment;
      ii) each measuring DNA fragment and each coding DNA fragment is generated by a separate DNA restriction endonuclease digest;
      iii) each coding DNA fragment recognizes a first nucleic acid probe; and
      iv) each measuring DNA fragment recognizes a second nucleic acid probe which may be the same as the first nucleic acid probe;
   b) electrophoresing through a gel a DNA sample to be analyzed;
   c) concurrently, in a different lane of the same gel, electrophoresing the sizing standard of step (a);
   d) visualizing the DNA bands in the gel obtained in step (c) by annealing one or more of said first or second nucleic acid probes, wherein said probes have been labeled;
   e) measuring the sizes of the DNA bands of both the electrophoresed DNA sample and the electrophoresed sizing standard;
   f) determining the expected sizes of said measuring fragments from the electrophoretic positions of said coding fragments; and
   g) determining the reliability of data obtained for said sample according to how closely the electrophoretic measurements obtained for said measuring fragments in said sizing standard correspond to their expected measurements.

2. The method of claim 1, wherein said measuring fragments differ in size by at least about 5%.

3. The method of claim 1, wherein said measuring fragments are obtainable by restriction endonuclease digestion of DNA from bacteriophage λ.

4. The method of claim 3, wherein said measuring fragments comprise a nucleotide sequence present in or complementary to a sequence present between nucleotide 33,783 and nucleotide 34,212 of bacteriophage λ.

5. The method of claim 1, wherein said measuring fragments and coding fragments are supplied separately and then combined to make up said standards.

6. The method of claim 1, wherein said coding fragments differ in size by at least about 5%.

7. The method of claim 1, wherein said coding fragments are obtainable by restriction endonuclease digestion of DNA from bacteriophage λ.

8. The method of claim 7, wherein said coding fragments comprise a nucleotide sequence present in or complementary to a sequence present between nucleotide 33,783 and nucleotide 34,212 of bacteriophage λ.

9. The method of claim 1, wherein said measuring fragments and said coding fragments are obtained from the same DNA molecules.

10. The method of claim 1, wherein said measuring fragments and said coding fragments are obtained from different DNA molecules.

* * * * *